United States Patent

Kamiyama et al.

[11] Patent Number: 5,873,829
[45] Date of Patent: Feb. 23, 1999

[54] DIAGNOSTIC ULTRASOUND SYSTEM USING HARMONIC ECHO IMAGING

[75] Inventors: Naohisa Kamiyama, Otawara; Yoshitaka Mine, Nishinasuno-Machi, both of Japan

[73] Assignee: Kabushiki Kaisha Toshiba, Kawasaki, Japan

[21] Appl. No.: 790,434

[22] Filed: Jan. 29, 1997

[30] Foreign Application Priority Data

Jan. 29, 1996 [JP] Japan .................................. 8-013266

[51] Int. Cl.[6] .......................................... A61B 8/00
[52] U.S. Cl. .......................................... 600/443; 600/458
[58] Field of Search .................................. 600/440, 441, 600/443, 458; 367/7

[56] References Cited

U.S. PATENT DOCUMENTS

| | | | |
|---|---|---|---|
| 5,014,710 | 5/1991 | Maslak | 600/441 |
| 5,224,483 | 7/1993 | Lipschutz | 600/440 |
| 5,255,683 | 10/1993 | Monaghan | 600/458 |
| 5,410,516 | 4/1995 | Uhlendorf et al. | 367/7 |
| 5,469,849 | 11/1995 | Sasaki et al. | 600/458 |
| 5,526,816 | 6/1996 | Arditi | 600/458 |
| 5,628,322 | 5/1997 | Mine | 600/458 |

FOREIGN PATENT DOCUMENTS

| | | |
|---|---|---|
| 0 357 164 | 3/1991 | European Pat. Off. . |
| 4-501518 | 3/1992 | Japan . |
| 5-84246 | 4/1993 | Japan . |
| 6-114059 | 4/1994 | Japan . |

OTHER PUBLICATIONS

IEEE Transactions on Ultrasonics, Ferroelectrics, and Frequency Control, vol. 39, No. 1, pp. 95–101, Jan. 1992, Christy K. Holland, et al., "In Vitro Detection of Cavitation Induced by a Diagnostic Ultrasound System".

J. Acoust. Soc. Am., vol. 91, No. 4, 2EA3, pp. 2324, Apr. 1992, Shiroh Saitoh, et al., "A Dual Frequency Ultrasonic Probe for Medical Application.".

Williams, A. et al "OTS Imaging . . . Using Non–Linear Scattering . . " PCT/GB91/00649 Published as WO91/15999 31 Oct. 1991.

*Primary Examiner*—Francis J. Jaworski
*Attorney, Agent, or Firm*—Oblon, Spivak, McClelland, Maier & Neustadt, P.C.

[57] ABSTRACT

In performing harmonic echo imaging, the necessity of changing modes is obviated, maneuverability is improved, and diagnostic information of the kinetics of a blood flow is provided with high reliability. A diagnostic ultrasound system provides, by scanning a cross section of an object with an ultrasonic beam signal, a normal B-mode image (the first tomographic image) of a tissue and a harmonic-mode image (the second tomographic image) of distribution information of an ultrasonic contrast medium injected into the object. The distribution information is obtained based on a non-fundamental frequency component (e.g., second harmonics) other than a fundamental frequency component of the ultrasonic beam signal. The system comprises a unit for scanning an ultrasonic beam signal along the cross section to acquire an echo. The scanning unit controls the scan so that the beam signal is scanned automatically and alternately for each raster in both the normal B-mode and the harmonic-mode. Preferably, the scan in the harmonic-mode precedes that of the normal B-mode. Image data of the first and second tomographic images are visualized on the basis of the echo.

32 Claims, 9 Drawing Sheets

| MODE | PARAMETERS | SCAN NUMBER : $m$ |
|---|---|---|
| HARMONIC | 2.5 MHz<br>NUMBER OF WAVES: 3<br>SOUND PRESSURE: 10 | (1),(3),(5),···(239) |
| NORMAL B | 3.75 MHz<br>NUMBER OF WAVES: 1<br>SOUND PRESSURE: 16 | (2),(4),(6),···(240) |

FIG. 8A  NORMAL B-MODE

FIG. 8B  HARMONIC-MODE (FREQUENCY OF DRIVING PULSES CHANGEABLE)

FIG. 8C  HARMONIC-MODE (FREQUENCY OF DRIVING PULSES CHANGEABLE)

DIAGNOSTIC ULTRASOUND SYSTEM USING HARMONIC ECHO IMAGING

BACKGROUND OF THE INVENTION

1. Field of the Invention

The present invention relates to a diagnostic ultrasound system, or more particularly, to a diagnostic ultrasound system having the ability to implement an imaging method referred to as "harmonic echo imaging" in which ultrasonic waves are scanned with an ultrasonic contrast medium injected into a patient body for the purpose of detection and quantitative assessment of perfusion of blood through a tissue.

2. Description of the Related Art

A diagnostic ultrasound system for producing an image signal through transmission and reception of ultrasonic waves has been employed in various ways owing to the noninvasiveness of ultrasonic waves in the past. Conventional diagnostic ultrasound systems produce tomographic images of a soft tissue of a living body by adopting ultrasonic pulse reflection imaging. This imaging method is noninvasive and produces a tomographic image of the tissue. Compared with other medical modalities such as diagnostic X-ray imaging, X-ray CT imaging, MRI, and diagnostic nuclear medicine imaging, the imaging method has many advantages: real-time display is possible, a compact and relatively inexpensive system can be constructed, patient exposure to X- rays or the like will not occur, and blood flow imaging is possible owing to ultrasonic Doppler imaging. The imaging method is therefore most suitable for diagnosis of the heart, abdomen, mammary gland, and urinary organs, and for diagnosis in obstetrics and gynecology. In particular, pulsation of the heart or motion of a fetus can be observed in real time through simple manipulation that is as simple as placing an ultrasonic probe on a patient's skin. Moreover, since patient exposure need not be cared about, screening can be carried out many times repeatedly. Furthermore, there is an advantage that a system can be moved to a bedside position for ready screening.

Under these circumstances, a new screening method for screening the heart or abdominal organs using ultrasonic waves has been developed in recent years. The method is such that ultrasonic waves are scanned with an ultrasonic contrast medium injected trans-venously, and a resultant image is used to evaluate the kinetics of a blood flow (Refer to, for example, U.S. Pat. No. 5,410,516 or Published Japanese Translation of PCT International Publication for Patent Application No. 4-501518. Since trans-venous injection of a contrast medium is less invasive than trans-arterial injection, the method for evaluating the kinetics of a blood flow is becoming popular. As an ultrasonic contrast medium, for example, a "5%-diluted human albumin with bubbles produced manually or using a sonicator" is known. The main component of the contrast medium is microscopic bubbles that act as a source of reflect ultrasonic waves. The larger the amount and concentration of injected contrast medium is, the larger the effect of contrast imaging is. However, since the bubbles are crushed due irradiation of ultrasonic waves, the time during which the effect of contrast imaging persists is shortened. Although a contrast medium characteristic of high persistency and high durability against sound pressure has been developed in recent years, the long-term persistence of the contrast medium in a human body predictably raises invasiveness.

A technique for detecting the presence or absence of blood flow in a diagnostic region by checking if luminance is intensified by a contrast medium has been adopted for the most fundamental diagnosis using an ultrasonic contrast medium. For more advanced diagnosis, a technique for acquiring information of a temporal change in spatial distribution of a contrast medium in a diagnostic region by detecting the spread of a change in luminance or the extent of intensification of luminance has been adopted. Also employed is a technique for obtaining information of a temporal change in spatial distribution by measuring a time required for an injected contrast medium to reach a region of interest (ROI) and a temporal change in luminance of echoes deriving from a contrast medium in a region of interest (time density curve (TDC)) or a maximum luminance. Processing of detecting a change in the level of ultrasonic echoes from a contrast medium which is necessary for those techniques is conventionally such that a change in the level of luminance of a B-mode image is checked merely visually, or image data of a plurality of frames are stored temporarily in a memory and then read in order to plot a histogram and thus quantitatively measure a change in level of echoes or plot a TDC.

In recent years, "harmonic echo imaging" has been devised as a technique for improving the effect of intensifying contrast echoes affected by an ultrasonic contrast medium. The harmonic echo imaging is based on the fact that microscopic bubbles of a contrast medium facilitate occurrence of an acoustic nonlinear phenomenon, that is, generation of reflected waves or echoes of nonlinear components or especially harmonics which are components other than the fundamental components of transmitted waves, and intended to distinguish in level echoes of harmonics from echoes emanating from an organ in a body that hardly generates harmonics. For example, reflected waves or echoes include fundamental components of transmitted waves and harmonics thereof stemming from a contrast medium. By displaying echoes remaining after the fundamental components are removed by a filter, the harmonics. That is, an image reflecting the extent of intensification due to the contrast medium can be obtained.

As mentioned above, using the harmonic echo imaging, once a relatively small amount of contract medium is administered, the presence or absence of the contrast medium in a region of interest, that is, the perfusion of blood, can be observed, and information helpful in diagnosis can be acquired.

However, for diagnosis based on harmonic echo imaging, when mere visualization based on the harmonic echo imaging is carried out, various drawbacks described below arise.

First, there is a problem concerning a diagnostic mode. Before administration (injection) of an ultrasonic contrast medium, a nonlinear effect exerted by an organ, vessel, or blood in the body is limited. Even if harmonic echo imaging (harmonic mode) is carried out in this state, almost no image information can be acquired. Therefore, when a region of interest is searched for and defined prior to administration of a contrast medium, the harmonic mode must be changed to a B-mode (normal B-mode) designed for interpreting a normal gray-scale tomographic image. Manipulation becomes time-consuming because of this mode change.

Secondly, there is a problem concerning the specification of a region to be observed. Assume that an ultrasonic contrast medium is administered and the magnitude of dying and shadowing by the contrast medium is observed. Since the effect of dying and shadowing decays gradually, the contour of an organ may not be observable. In this case, if a region to be observed becomes inconsistent with an object organ of observation on a tomographic image by accident, an observer may not be aware of the fact. Since this kind of accident is predicted, the results of diagnosis are naturally accompanied with a concern about reliability.

Thirdly, there is a problem attributable to microscopic bubbles that are the main component of an ultrasonic contrast medium. It is known that the microscopic bubbles are very delicate and vanish with irradiation of specific ultrasonic waves. As for this matter, sound pressure in the presence of ultrasonic waves capable of demolishing bubbles has been reported in, for example, a thesis entitled "In vitro detection of cavitation induced by a diagnostic ultrasound system" written by Christy K. Holland et al. (IEEE Trans. on Ultrason. Ferroelec. and Freq. Cont., Vol. 39, No. 1, January 1992). This report was verified by an experiment conducted by the present inventor. It has been confirmed that the sound pressure of a level usable in clinical practice may cause collapse of bubbles.

Furthermore, it is known that bubbles have a frequency characteristic dependent on the size (diameter) of an incident ultrasonic beam in the presence of which a sound pressure is detected. In particular, at a resonant frequency, bubbles vibrate with a large amplitude and eventually collapse or cavitate. If vanishing of bubbles due to irradiation of ultrasonic waves occurs at a rate that is higher than the speed of supplying a contrast medium (microscopic foams), echoes intensified by the contrast medium cannot be acquired. Consequently, proper values of physical quantities serving as conditions for transmission such as the sound pressure in the presence of transmitted ultrasonic waves, the frequency of the transmitted ultrasonic waves, the transmission rate thereof, the aperture of a probe for transmission, and the focus of the transmitted ultrasonic waves must be taken into account. However, prior arts have not taken such a point into consideration.

SUMMARY OF THE INVENTION

The present invention attempts to overcome the foregoing drawbacks. A major object of the present invention is to provide highly efficient operation and reliable images of the harmonic-mode. A practical object of the present invention is to obviate the necessity of changing modes, improve maneuverability, and provide highly reliable diagnostic information of the kinetics of a blood flow.

For accomplishing the above object, as one aspect of the present invention, there is provided a diagnostic ultrasound system providing by scanning a cross section of an object with an ultrasonic beam signal, a first tomographic image of a tissue in the cross section, and a second tomographic image of distribution information of an ultrasonic contrast medium in the cross section. The medium is injected into the object and said distribution information is obtained based on a non-fundamental frequency component other than a fundamental frequency component of the ultrasonic beam signal. The system comprises: means for scanning an ultrasonic beam signal along the cross section of the object to acquire an echo of the ultrasonic beam signal emanated from the cross section, said scanning means including means for controlling the scan so that the ultrasonic beam signal is scanned automatically for each raster of the scanned ultrasonic beam signal in both a first imaging mode for obtaining the first tomographic image and a second imaging mode for obtaining the second tomographic image. The system also comprises first means for producing image data of the first tomographic image on the basis of the echo, second means for producing image data of the second tomographic image on the basis of the echo, and means for visualizing the image data of the first and second tomographic images.

Preferably, said visualizing means comprises a monitor and means for superimposedly displaying on the monitor the image data of the second tomographic image on the image data of the first tomographic image. For example, said displaying means includes an element for providing a color to the image data of the second tomographic image.

Preferably said scan-controlling means includes an element repeating the scan for each raster alternately and automatically between the first and second imaging modes. Also preferred is that said scan-controlling means includes an element switching the scan between the first and second imaging modes frame by frame.

Preferably, said scan-controlling means comprises means for changing a transmitting condition of the ultrasonic beam signal transmitted every imaging mode between the scan in the first and second imaging modes. The transmitting condition includes at least one of a transmission frequency of the ultrasonic beam signal, a sound pressure of the ultrasonic beam signal, the number of waves of the ultrasonic beam signal, a waveform of the ultrasonic beam signal, a focal point of the ultrasonic beam signal, a transmission rate of the ultrasonic beam signal, and a transmission aperture of an ultrasonic probe transmitting the ultrasonic beam signal.

For example, said the transmitting condition is the transmission frequency and the second imaging mode is smaller in the transmission frequency than the first imaging mode. It is also preferred that said transmitting condition is the sound pressure and that the second imaging mode creates less sound pressure than the first imaging mode.

Preferably, said scan-controlling means includes an element repeating the scan for each raster alternately and automatically between the first and second imaging modes, and said repeating element is constructed so that, for each raster, the scan of the ultrasonic beam signal in the second imaging mode precedes the scan of the ultrasonic beam signal in the first imaging mode. In such case, said scan-controlling means comprises means preferably for changing a transmitting condition of the ultrasonic beam signal transmitted every imaging mode between the scan in the first and second imaging modes.

In another aspect of the present invention, there is provided a diagnostic ultrasound system provided by scanning a cross section of an object with an ultrasonic beam signal, a first tomographic image of a tissue in the cross section, and a second tomographic image of distribution information of an ultrasonic contrast medium in the cross section. The medium is injected into the object and said distribution information is obtained based on a non-fundamental frequency component other than a fundamental frequency component of the ultrasonic beam signal. The system comprises: an ultrasonic probe transmitting the ultrasonic beam signal to the object and receiving an echo of the ultrasonic beam signal reflected from the object; an ultrasonic transmitting unit including a first pulser for driving the ultrasonic probe in a first imaging mode for obtaining the first tomographic image and a second pulser for driving the ultrasonic probe in a second imaging mode for obtaining the second tomographic image; a switch for selectively activating either one of the first or second pulser in the ultrasonic transmitting unit; and a control unit for controlling the scan so that the ultrasonic beam signal is scanned automatically in both the first and second modes for each raster of the scanned ultrasonic beam signal.

In this case, also preferred is that said control unit comprises a control element repeating the scan for each raster automatically and alternately between the first and second imaging modes, the second imaging mode preceding the first imaging mode in the order of the scan for each raster. For example, said control unit comprises a control element changing a transmitting condition of the ultrasonic beam signal every imaging mode between the scan in the first and second imaging modes.

According to the present invention, a section of a desired region is scanned with ultrasonic waves, at least two scans are carried out along the same scanning line in the normal B-mode and harmonic mode, and echoes are acquired from the section. A normal B-mode image and harmonic-mode (one kind of B-mode) image can therefore be produced at substantially the same time instant in units of a transmission rate or frame rate. Consequently, the contour of a tissue in a patient body and the kinetics of a blood flow which is visualized owing to the nonlinear effect of an ultrasonic contrast medium can be observed simultaneously from the normal B-mode image and harmonic-mode image, respectively. In the harmonic echo imaging, the necessity of changing modes can be obviated, maneuverability can be improved, and diagnostic information of the kinetics of a blood flow can be provided with high reliability.

DESCRIPTION OF THE PREFERRED EMBODIMENTS

An embodiment of the present invention will be described with reference to FIGS. 1 to 7. A diagnostic ultrasound system in accordance with this embodiment adopts a configuration for identifying an abnormal region according to diagnostic information of the state of blood flow into the heart, or more particularly, the left ventricular muscle. However, the diagnostic ultrasound system of the present invention is not necessarily limited to such application that the state of a blood flow into the cardiac muscle is an object of diagnosis.

Figure 1:
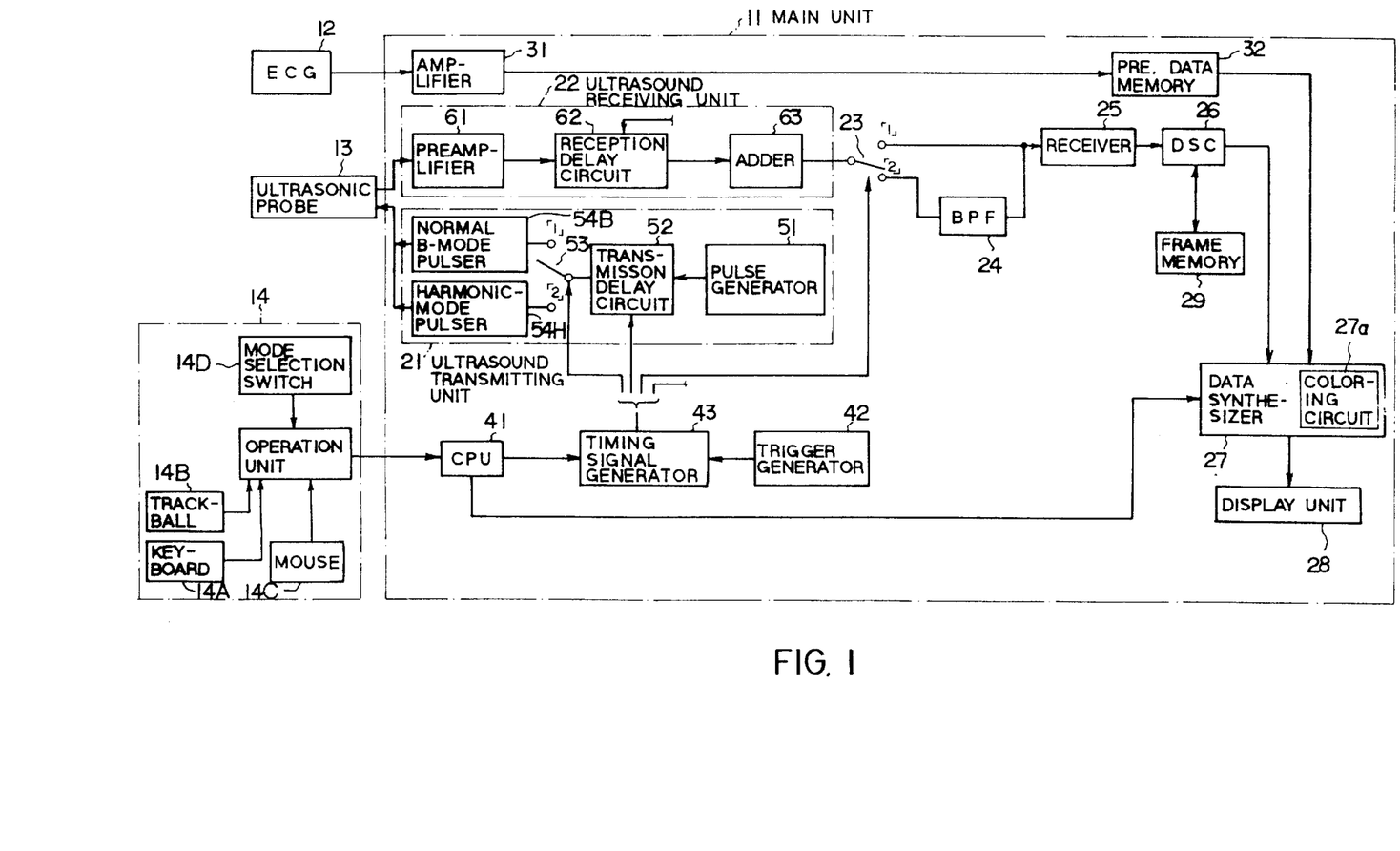
FIG. 1 is a schematic block diagram showing the overall configuration of a diagnostic ultrasound system in accordance with the present invention.

The diagnostic ultrasound system shown in FIG. 1 comprises a main unit 11 that functions as a control center of the whole system, an electrocardiograph (ECG) 12 connected to the main unit 11, an ultrasonic probe 13 connected to the main unit 11, and an operation unit 14 connected to the main unit 11. The operation unit 14 is used to give various instructions or information entered by an operator to the main unit 11. The operation unit 14 includes a keyboard 14A as well as a mouse 14B and trackball 14C for use in defining a region of interest (ROI), and a mode selection switch 14D for changing diagnostic modes manually.

The ultrasonic probe 13 includes piezoelectric transducers made of piezoelectric ceramic or the like as electromechanical bilateral converting elements. A plurality of piezoelectric transducers are set in an array and incorporated in the distal part of the probe, thus constructing the phased array type probe 13. The probe 13 converts driving voltage pulses applied by the main unit 11 into ultrasonic pulses and transmits the ultrasonic pulses in a desired direction in a patient body. Moreover, the probe 13 converts ultrasonic echoes reflected from the patient body into a signal with corresponding voltages.

The main unit 11 comprises an ultrasound transmitting unit 21 and ultrasound receiving unit 22 which are connected to the probe 13 as well as a selection switch 23, bandpass filter (BPF) 24, receiver 25, digital scan converter (DSC) 26, data synthesizer 27, and display unit 28 which are placed in that order on the output stage of the ultrasound receiving unit 22. The main unit 11 further comprises an amplifier 31 and reference data memory 32 which are connected in that order on the output stage of the ECG 12. A frame memory 29 is connected to the DSC 26. The main unit 11 further comprises a central processing unit (CPU) 41 for receiving operation data entered at the operation unit 14 and also includes a trigger generator 42 and timing signal generator 43 which play a pivotal role in the control center.

The ultrasound transmitting unit 21 includes a pulse generator 51, transmission delay circuit 52, selection switch 53, normal B-mode pulser 54B, and harmonic-mode pulser 54H. Herein, the "normal B-mode" (serving as the first imaging mode of the invention) is a mode for producing a normal gray-scale tomographic image without the employment of harmonic echo imaging, and differentiated from a "harmonic-mode" (serving as the second imaging mode of the invention) that is also a B-mode in terms of the principles but based on harmonic echo imaging basically intended for imaging of harmonics.

The pulse generator 51 generates rated pulses of a frequency fr [Hz] of, for example, 5 k Hz (cycle: 1/fr [sec.]). The rated pulses are distributed into transmission channels and sent to the transmission delay circuit 52. A timing signal used to determine a delay time is sent from the timing signal generator 43 to the transmission delay circuit 52 for each transmission channel. This causes the transmission delay circuit 52 to delay the rated pulses for the same channel by a commanded delay time. As a result, the ultrasonic waves transmitted from the ultrasonic probe 13 are converged in the form of a beam inside the patient body and have the transmission directivity thereof set to a commanded scan direction.

The selection switch 53 included in the ultrasound transmitting unit 21 selects either of two electronic switch paths according to a switching signal sent from the timing signal generator 43. The normal B-mode pulser 54B is connected to one switch terminal "1" of the selection switch 53, and the harmonic-mode pulser 54H is connected to the other switch terminal "2" thereof. Owing to the selective switching at the selection switch 53, rated pulses delayed by a delay time are supplied to the normal B-mode pulser 54B or harmonic-mode pulser 54H for each transmission channel.

The normal B-mode pulser 54B applies driving voltage pulses to the transducers of the probe 1 3 belonging to the same channel according to the timing of the rated pulses received via the selection switch 53. With this excitation, ultrasonic waves are transmitted to the patient body from the plurality of piezoelectric transducers of the ultrasonic probe 13. Beam forming is then, as mentioned above, carried out according to a delay time pattern within the patient body. For transmission in the harmonic mode, the selection switch 53 is switched over to the switch terminal "2". This causes the harmonic-mode pulser 54H to operate in the same manner.

The parameters for the driving voltage pulses (normal transmission pulses) for the normal B-mode and the driving voltage pulses (harmonic transmission pulses) for the harmonic-mode, which are associated with the pulsers 54B and 54H, are set to be optimal for the respective modes. This setting is illustrated in FIGS. 2A to 2C and 5.

Figure 2A:
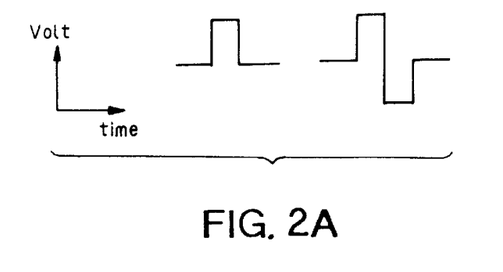
FIGS. 2A to 2C are diagrams showing examples of waveforms of various driving pulses.
Figure 2B:
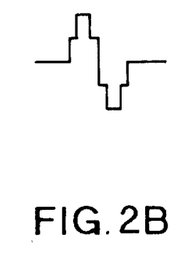
Figure 2C:
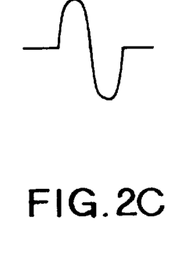

To begin with, a difference in waveform between a normal transmission pulse and harmonic transmission pulse will be described in conjunction with FIGS. 2A to 2C. FIG. 2A show two waveforms assumed by the normal transmission pulse. This pulse is a rectangular wave of one polarity or opposite polarities to be generated by switching voltages of two values using a switch element. A pulser for creating these waveforms has the advantage that the circuit scale is small and the power consumption is small. FIG. 2B shows an example of a harmonic transmission pulse. This pulse is produced by, for example, setting a plurality of switchable voltage values in the pulser 54H and switching voltages of the values using a switch element. FIG. 2C shows another example of the harmonic transmission pulse. This sinusoidal wave is produced by a class-A operation amplifier. The harmonic transmission pulses shown in FIGS. 2B and 2C contain fewer harmonics than a normal rectangular wave and are therefore suitable for the harmonic mode in which the fewest possible harmonics are preferably contained in a transmitted wave.

Figure 5:
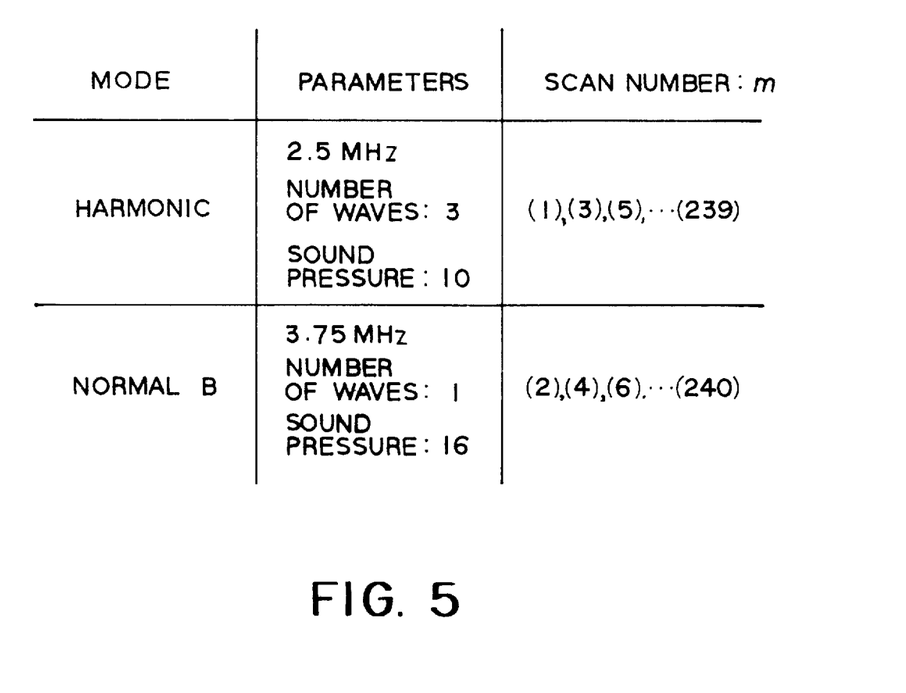
FIG. 5 is a table for explaining scan control for two modes and examples of parameters.

The frequencies of driving voltage pulses (transmission pulses) generated by the normal B-mode pulser 54B and harmonic-mode pulser 54H, the numbers of waves thereof, and sound pressures in the presence of the pulses are set to optimal values in the normal and harmonic modes, for example, to values listed in FIG. 5 in this embodiment. These driving conditions may be set on a fixed basis in each pulser or may be changeable according to a command sent from the CPU 41.

The frequency of driving voltage pulses is set to, for example, 3.75 MHz for the normal B-mode and 2.5 MHz for the harmonic mode. If the frequency of driving voltage pulses in the harmonic mode were the same as that in the normal B-mode or, for example, 3.75 MHz, received harmonics would have a frequency as high as 7.5 MHz. Consequently, echoes would be affected by in vivo decay or the like, and reception sensitivity would deteriorate. As the frequency increases, the conditions for circuit design become more strict. To avoid this, the frequency of driving voltage pulses in the harmonic mode is made lower than that in the normal B-mode. By contrast, if a lower frequency suitable for the harmonic mode were set as the frequency of driving voltage pulses used in common between both the modes, the normal B-mode would result in a coarse speckle pattern. This means that deterioration of image quality cannot be avoided. It is therefore very effective when appropriate frequencies are set for the respective modes as mentioned above.

The number of waves is set to, for example, "1" for the normal B-mode and "3" for the harmonic mode. This is because sensitivity is expected to improve in the harmonic mode by increasing the number of waves, though spatial resolution (in a depth direction) deteriorates.

The sound pressure is set to, for example, "16" for the normal B-mode (coded driving voltage value: relative value) and "10" for the harmonic mode. These values are determined in consideration of the extent of vanishing of bubbles or the like.

Incidentally, the aforesaid optimal conditions for driving in each mode may include a focus of transmitted waves, an aperture of a probe for transmission, and a transmission rate. The focus of transmitted waves is, for example, set in consideration of sensitivity in deeper ranges so that the focus is positioned at the center in a depth direction for the normal B-mode and at a deeper region in the depth direction for the harmonic mode. The aperture for transmission is set in consideration of the uniformity of spatial distribution of sound pressures so that it becomes smaller in the harmonic mode than in the normal B-mode. The transmission rate is set so that it becomes lower in the harmonic mode than in the normal B-mode. Any two or more of these conditions for driving (transmission) may be adopted in combination for more proper control of transmission in each mode.

In this embodiment, transmission using the normal B-mode pulser 54B shall be referred to as "normal transmission," while transmission using the harmonic-mode pulser 54H shall be referred to as "harmonic transmission."

Ultrasonic pulses transmitted from the ultrasonic probe 13 are reflected by a plane in a patient body for which acoustic impedance is discontinuous. Reflected ultrasonic waves are received again by the probe 13 and converted into a signal with corresponding voltages. The signal is output from the probe 13 for each reception channel and fetched into the ultrasound receiving unit 22.

The ultrasound receiving unit 22 comprises a preamplifier 61, reception delay circuit 62, and adder 63 in that order from the input stage thereof. The preamplifier 61 and reception delay circuit 62 have the same numbers of amplifiers and delay circuits respectively as the number of reception channels. A delay time pattern to be followed by the reception delay circuit 62 is given as a trigger pattern by the timing signal generator 43 according to desired reception directivity. The signal is, for each channel, amplified by the preamplifier 61, and provided with a delay time by the reception delay circuit 62. Signals for all channels are then added up by the adder 63. As a result, a received beam is formed by calculation with components reflected from a direction matching the desired reception directivity intensified. Transmission directivity and reception directivity are taken into account comprehensively, whereby a comprehensive ultrasonic beam to be transmitted and received is formed.

The output terminal of the adder 63 is connected to the common terminal of the selection switch 23. The selection switch 23 is an electronic switch and includes two switch terminals "1" and "2" that are switched in response to a switching signal supplied from the timing signal generator 43. One switch terminal "1" is associated with the normal B-mode and the other switch terminal "2" is associated with the harmonic mode. The switch terminal "1" is routed directly to the DSC 26 via the receiver 25, while the other switch terminal "2" is routed to the receiver 25 via the harmonic bandpass filter (BPF) 24 and then to the DSC 26. The BPF 24 has a passband thereof set so as to pass only nonlinear components (for example, second harmonics) of a signal having undergone delay addition (beam forming) which are necessary for harmonic echo imaging.

Hereinafter, reception of a signal by bypassing the BPF 24 shall be referred to as "normal reception," while reception of a signal via the BPF 24 shall be referred to as "harmonic reception."

The receiver 25 includes a logarithmic amplifier, envelope detector, and an A/D converter which are not illustrated. In either the normal B-mode or harmonic echo mode, echo data originating from a direction matching reception directivity is produced digitally and sent to the DSC 26. The DSC 26 converts echo data conformable to an ultrasonic scanning system into echo data conformable to a standard television scanning system, and sends the resultant echo data to the data synthesizer 27. The echo data output from the DSC 26 is stored frame by frame in the frame memory 29.

An electrocardiographic signal detected by the electrocardiograph (ECG) 12 is sent to the reference data memory 32 via the amplifier 31. The reference data memory 32 produces reference data such as an electrocardiogram corresponding to the electrocardiographic signal and sends the reference data to the data synthesizer 27.

The data synthesizer 27 forms image data of the normal B mode and image data of the harmonic mode, synthesizes image data of the modes and reference data according to a control signal concerning a display form which is sent from the CPU 41, and thus produces an image of one frame. The data synthesizer 27 includes a coloring circuit 27A for providing color information of red, for example, to image data of harmonic-mode images. The frame image data is read successively by the display unit 28. The display unit 28 causes a built-in D/A converter thereof to convert received data into an analog quantity, and displays the analog quantity on a TV monitor. In a synthetic form of image data of both the modes, typically, the image data of one mode and that of the other mode are displayed side by side or the image data of one mode is superposed on that of the other mode. As a result, the spatial distribution of a tissue of a patient body is visualized in the normal B-mode, while the spatial distribution of an injected contrast medium is visualized in the harmonic mode.

The CPU 41 normally runs a given main program. When receiving a scan start command resulting from automatic mode change from the operation unit 14, the CPU 41 executes the processing described in FIG. 3 in response to the command. Scan control is then automatically instructed to the timing signal generator 43. When receiving an ROI setting signal from the trackball 14C or the like, the CPU 41 sends graphic data concerning a region of interest (ROI) to the data synthesizer 27 and carries out the processing of superposing an ROI lineation on a display image. When a display form on the TV monitor of the display unit 28 is commanded at the keyboard 14A or the like, the CPU 41 sends a signal for commanding the display form to the data synthesizer 27. Furthermore, when a diagnostic mode is designated using the mode selection switch 14D, the CPU 41 commands either mode (normal B-mode or harmonic mode) forcibly to the timing signal generator 43.

Based on the command sent from the CPU 41, the timing signal generator 43 sends a delay time pattern concerning a combination of normal B-mode scan and harmonic-mode scan (or selected one thereof) and a timing signal concerning switching to each of the transmission delay circuit 52, reception delay circuit 62, and selection switches 53 and 23.

The operations in this embodiment will be described.

In general, electronic sector scanning is often employed in producing frames of an ultrasonic tomographic image. The scanning method is performed using, for example, 120 rasters (scanning lines) traced by continuous scan performed by changing the direction (angle) of a scanning line. The description will now proceed on the assumption that the scanning method is adopted.

Figure 3:
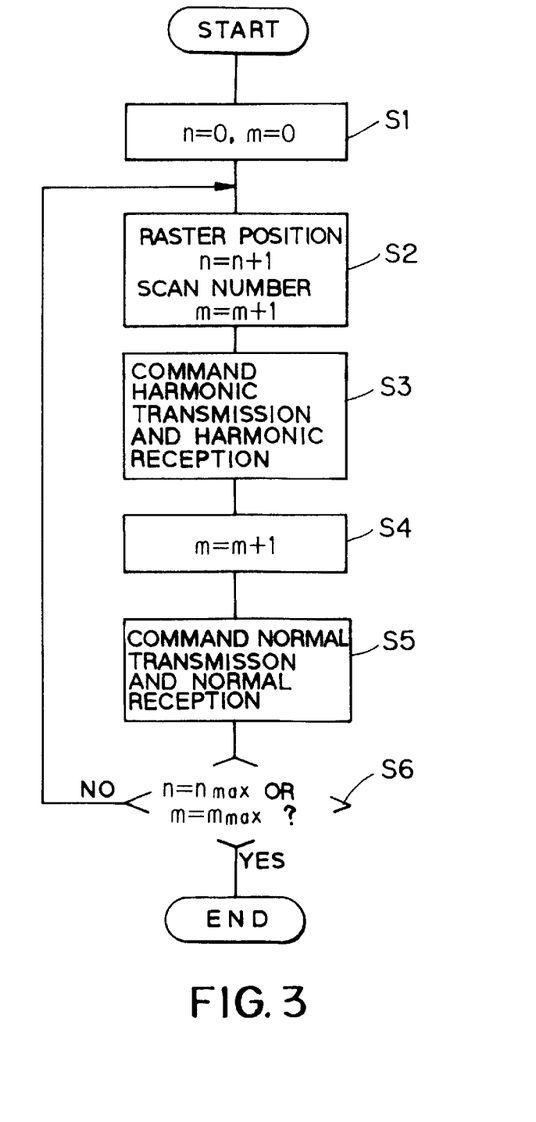
FIG. 3 is a schematic flowchart describing scan control for two modes.

The CPU 101 starts the processing described in FIG. 3 in response to a command sent from the operation unit 14. Assuming that a parameter indicating a raster position is n, and a parameter indicating a scan number is m, the parameters n and m are initialized to 0 at step S1 in FIG. 3.

At step S2, the parameters n and m are incremented by one to be n+1 and m+1 respectively. An initial raster position n=1 is then computed, and the scan number m=1 is named. Thereafter, at step S3, harmonic transmission and harmonic reception are commanded to the timing signal generator 43. Harmonic-mode scan under raster position n=1 and scan number m=1 is executed prior to normal B-mode scan to be carried out at the same raster position (See FIGS. 4 and 5).

Responsive to the scan start command for the harmonic-mode, the selection switch 53 in the ultrasound transmitting unit 21 and the selection switch 23 on the receiving side of the main unit are switched synchronously over to the harmonic-mode sides thereof. This causes the harmonic-mode pulser 54H on the transmitting side of the main unit to operate and the BPF 24 on the receiving side thereof to join the circuit. Thus, transmission and reception are carried out in the harmonic mode, and data concerning the spatial distribution of an ultrasonic contrast medium injected transvenously to a patient body is provided by the receiver 25.

Next, steps S4 and S5 are executed successively. At step S4, the scan number m alone is incremented by one to be m+1. At step S5, normal transmission and normal reception are commanded to the timing signal generator 43. The selection switches 53 and 23 are switched synchronously over to the normal B-mode sides thereof in response to a switching signal output from the timing signal generator 43. Normal B-mode scan under raster position n=1 and scan number m=2 is executed at the same raster position successive to the harmonic-mode scan (See FIGS. 4 and 5).

In response to the scan start command for the normal B-mode, the selection switch 53 in the ultrasound transmitting unit 21 and the selection switch 23 on the receiving side of the main unit are switched synchronously over to the normal B-mode sides thereof. This causes the normal B-mode pulser 54B on the transmitting side of the main unit to operate and the BPF 24 on the receiving side thereof to separate from the circuit. Thus, transmission and reception are carried out in the normal B-mode, and data concerning the spatial distribution of a tissue in a patient body is provided by the receiver 25.

Next, the CPU 41 passes control to step S6, judges whether or not raster number $n=n_{max}$ (for example, 120 lines) or scan number $m=m_{max}$ (for example, $240=120\times2$) is established, and thus determines whether or not scan control should be terminated. If the judgment is made in the negative, control is returned to step S2. The foregoing sequence is repeated.

Figure 4:
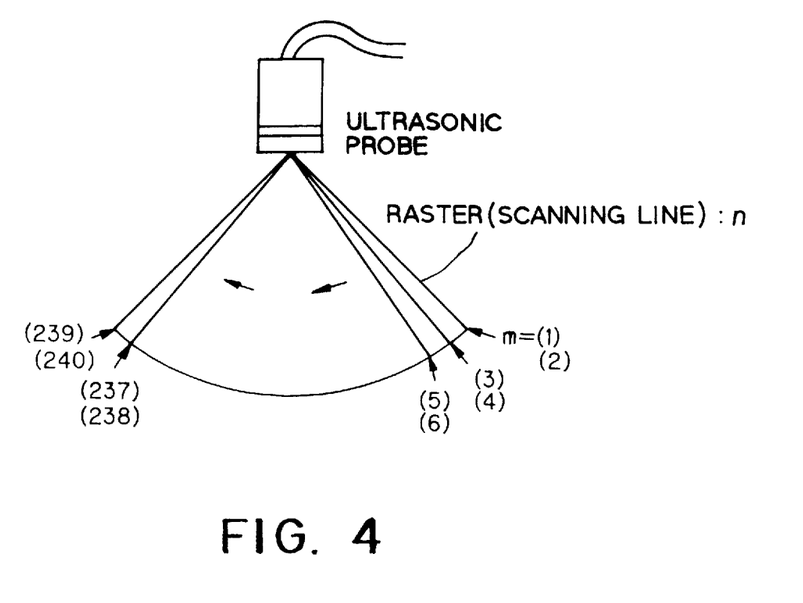
FIG. 4 is an explanatory diagram of scan control for two modes.

Owing to the aforesaid scan control, as shown in FIGS. 4 and 5, two transmissions and two receptions, that is, harmonic-mode transmission and reception and normal B-mode transmission and reception, are carried out along a raster (scanning line) in one direction. Rasters are changed successively. Transmissions and receptions in two modes are carried out for each raster. As a result, data of one frame of normal B-mode image and data of one frame of harmonic-mode image are produced by carrying out 240 scans. A time difference in data acquisition along the same raster between the two modes is 1/fr sec. Thus, high real-time imaging capability is maintained.

Echo data acquired by performing scanning alternately in two modes is sent successively to the memory synthesizer 27 via the DSC 26. The data synthesizer 27 differentiates normal B-mode image data and harmonic-mode image data, which are sent alternately and substantially in real time, from each other. Image data of both modes is synthesized into one frame according to a display form designated at that time, and displayed on the TV monitor of the display unit 28.

Figure 6:
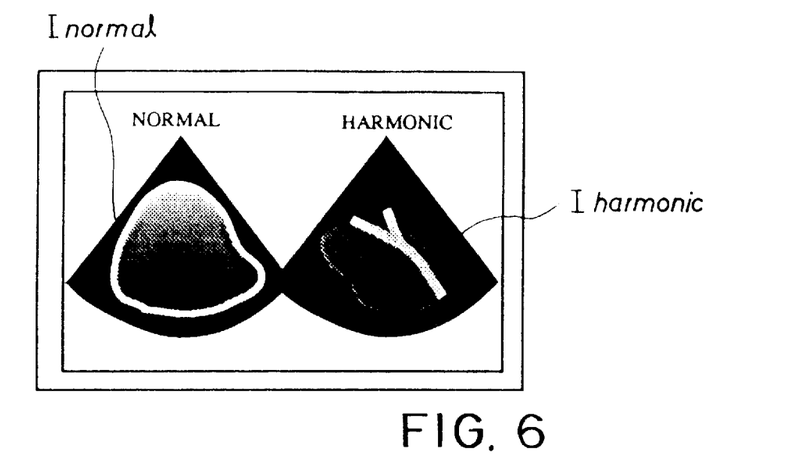
FIG. 6 is a diagram showing an example of display images of two modes.
Figure 7:
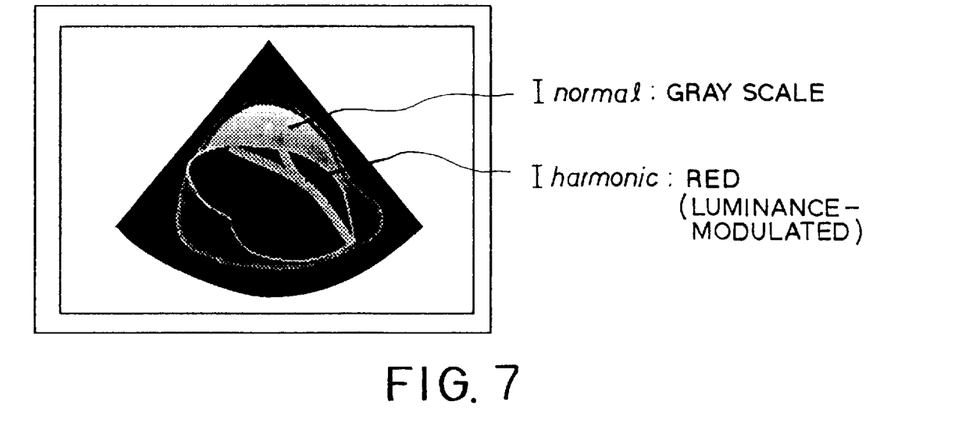
FIG. 7 is a diagram showing another example of display images of two modes.

FIGS. 6 and 7 show examples of the display form. FIG. 6 shows an example of displaying a normal B-mode image $I_{normal}$ (a tomographic image representing the spatial distribution of a tissue) and a harmonic-mode image $I_{harmonic}$ (a tomographic image representing the color spatial distribution of an ultrasonic contrast medium) in one screen separately side by side, as a dual image. FIG. 7 shows an example of displaying both the images $I_{normal}$ and $I_{harmonic}$ by superposing one image on the other in one screen. In the display form of FIG. 7, the quality of discernible and recognizable display should preferably be improved so that the normal B-mode image $I_{normal}$ can be displayed in gray scale, and the harmonic-mode image $I_{harmonic}$ can be displayed in color (for example, in red with a different luminance level proportional to the concentration of a contrast medium).

As mentioned above, in addition to a harmonic-mode image, a normal B-mode tomographic image is always displayed on the same monitor. Therefore, even when a region of interest must be searched for and defined prior to administration of a contrast medium, it is unnecessary to change a mode to the B-mode (normal B-mode). Maneuverability improves drastically.

After an ultrasonic contrast medium is administered, the effect of dying and shadowing decays gradually with the passage of time. Hence, in the case of a harmonic-mode image, the contour of an organ may not observable. Nevertheless, since a normal B-mode tomographic image is also displayed on the same monitor, even if a region to be observed becomes inconsistent with an object organ of observation, an observer can be aware of the Consequently, the reliability of the results of diagnosis improves.

Furthermore, the conditions for transmission in the harmonic mode such as the sound pressure in the presence of transmitted ultrasonic waves, the frequency thereof, the transmission rate, the aperture of a probe for transmission, and the focus of the transmitted ultrasonic waves are actively differentiated from those in the normal B-mode, and set to more appropriate quantities. Scanning can therefore be carried out in consideration of the vanishing of an ultrasonic contrast medium due to collapse thereof. This results in a highly precise and reliable image of the kinetics of a blood flow.

According to this embodiment, as far as the same raster is concerned, harmonic-mode transmission and reception always precedes normal B-mode transmission and reception. This is effective in increasing the effect of intensifying nonlinear signal components stemming from a contrast medium. If normal B-mode transmission and reception were carried out previously, microscopic bubbles of a contrast medium residing on rasters to be traced during transmission are crushed due to ultrasonic irradiation occurring in the normal B-mode. Consequently, part or a majority of the bubbles vanish. Even if harmonic-mode transmission and reception are carried out along the rasters, since few bubbles exist, the effect of signal intensification dependent on an acoustic nonlinear effect deteriorates. This kind of event can be avoided owing to the precedence of harmonic-mode scan. In the harmonic mode, the great effect of intensifying non-fundamental components can be exerted and the data of spatial distribution of a contrast medium can be acquired reliably.

Next, a variant of the present invention will be described.

Figure 8A:
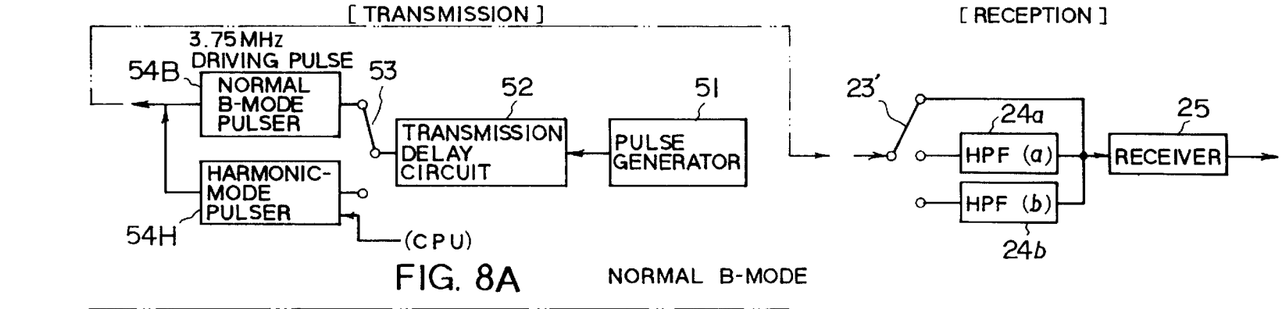
FIGS. 8A to 8C are partial block diagrams showing variants of transmitting and receiving systems.
Figure 8B:
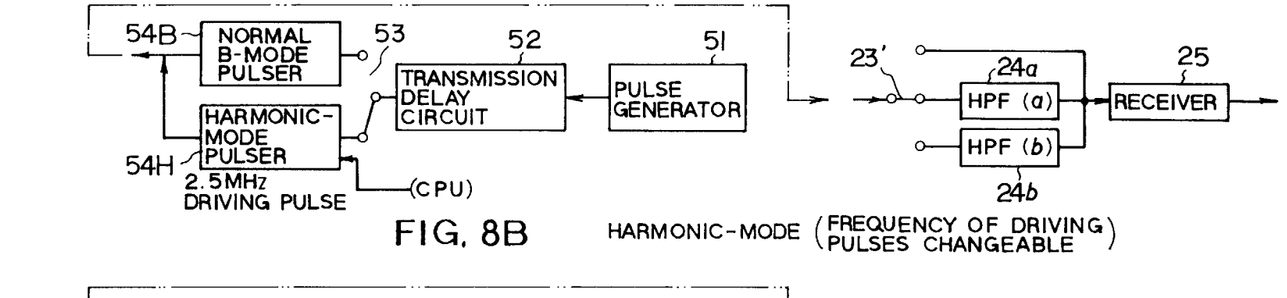
Figure 8C:
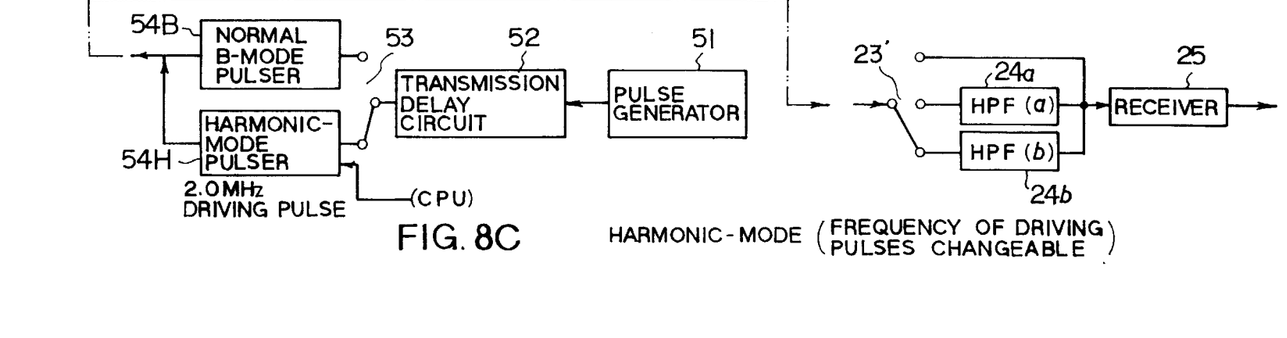

FIGS. 8A to 8C show the circuitry for changing a frequency of the driving voltage pulses generated by a pulser and the additional circuitry of a receiving system. As illustrated, the frequency of the driving voltage pulses generated by the normal B-mode pulser 54B is set to 3.75 MHz on a fixed basis. However, the frequency of driving voltage pulses generated by the harmonic-mode pulser 54H can be changed from 2.5 MHz to 2.0 MHz or vice versa in response to a control signal sent from the CPU 41. Accordingly, a selection switch 23' in the receiving system has three switch terminals. The first switch terminal is connected directly to the receiver 25. The second and third switch terminals are connected to the receiver 25 via HPFs (high-pass filters) 24a and 24b, respectively. BPFs (band-pass filters) may be used for HPFs. One HPF 24a has the cutoff frequency thereof set to a frequency permitting passage of harmonics, of which frequency 5 MHz is twice the frequency 2.5 MHz of the fundamental components, for example, to 4.8 Mhz. The other HPF 24b has the cutoff frequency thereof set to a frequency permitting passage of harmonics, of which frequency 4.0 MHz is twice the frequency 2.0 MHz of the fundamental components, for example, to 3.8 MHz.

In the normal B-mode, the selection switch 53 on the transmitting side of the main unit is switched over to the normal B-mode pulser 54B. In synchronization, the selection switch 23' on the receiving side thereof is switched over to the first switch terminal thereof. Thus, normal transmission and normal reception can be carried out properly.

In the harmonic mode, the frequency of driving voltage pulses is set to 2.5 MHz or 2.0 MHz. When 2.5 MHz is selected, the selection switch 53 on the transmitting side of the main unit is switched over to the harmonic mode pulser 54H. In synchronization, the selection switch 23' on the receiving side thereof is switched over to the second switch terminal. Consequently, the HPF 24b on the receiving side thereof, which is associated with the frequency of driving voltage pulses, 2.5 MHz, is selected, and harmonic transmission and harmonic reception are carried out properly. When 2.0 MHz is selected, the selection switch 53 on the transmitting side of the main unit is switched over to the harmonic mode pulser 54H. In synchronization, the selection switch 23' on the receiving side thereof is switched over to the third switch terminal. Consequently, the HPF 24c on the receiving side thereof which is associated with the frequency of driving voltage pulses, 2.0 MHz is selected.

Since the frequency of driving voltage pulses is thus changed from one to another mode by mode, the influence of in vivo decay occurring in the harmonic mode can be avoided, and deterioration of image quality occurring in the normal B-mode can be prevented reliably. Even in the same harmonic mode, since the frequency of driving voltage pulses can thus be adjusted finely, higher-precision information of the kinetics of a blood flow can be acquired.

The number of changeable frequencies of driving voltage pulses for the harmonic mode is not limited to two. Three or more appropriate frequencies may be adopted. In this case, the number of HPFs is increased accordingly.

Figure 9:
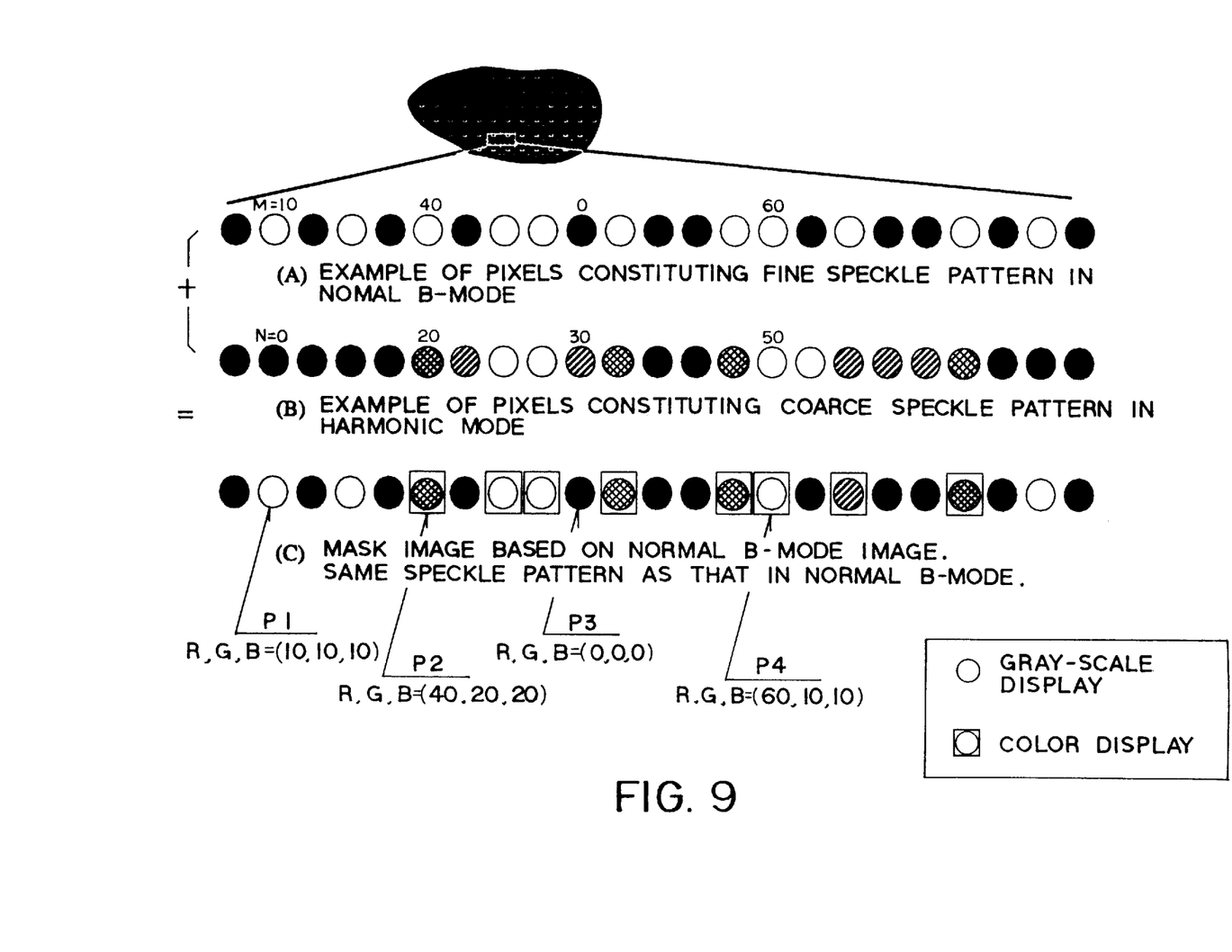
FIG. 9 is a diagram for explaining a variant of superposition display.

FIGS. 9 illustrates a variant concerning image display, showing examples of two images produced in the normal B-mode and harmonic mode by superposing one image on another. FIG. 9(A) is a conceptual diagram of some of pixels constituting a normal B-mode gray-scale image and shows a fine speckle pattern. FIG. 9 illustrates the concept of some pixels constituting a harmonic-mode image. Normally, the power of a signal used to produce a harmonic-mode image, that is, extracted harmonics, is much weaker than that of fundamental components. Besides, since the signal is passed through a dedicated filter in each of the transmitting and receiving systems, the signal-to-noise ratio and distance resolution of the signal deteriorate. In the harmonic mode, therefore, the pixels constitute a coarse speckle pattern as shown in FIG. 9(B).

In this variant, as shown in FIG. 7 referenced previously, when one image is superposed on another, image data acquired in the harmonic mode will not be superposed on image data acquired in the normal B-mode as it is. To obtain superposed (masked) image data as shown in FIG. 9(C), the data synthesizer 27 executes the processing represented in FIG. 10 pixel by pixel in response to a superposing command from the CPU 41.

Figure 10:
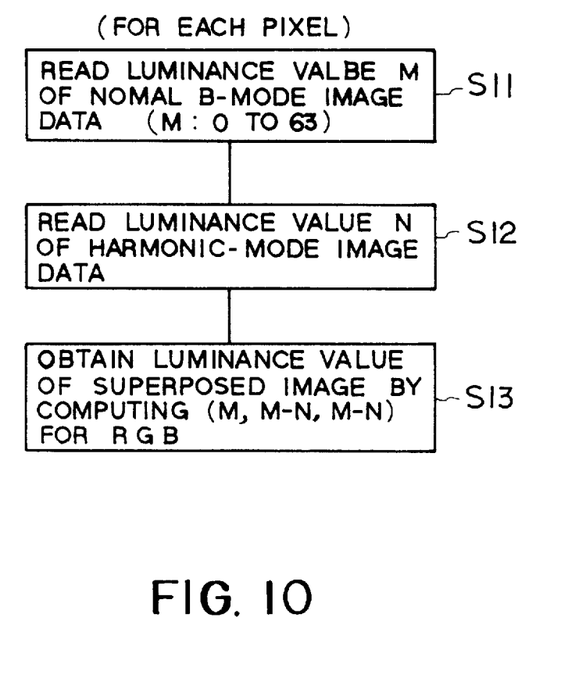
FIG. 10 is a schematic diagram showing the processing to obtain a superposed image shown in FIG. 9.

At step S11, the data synthesizer 27 reads the luminance (brightness) value M of each pixel of a normal B-mode image data. The value M ranges, for example, over the relative values of 0 to 63. Then at step S12, likewise, the synthesizer 27 reads the luminance value N of RGB color elements of each pixel of a harmonic-mode image data having color information. Then at step S13, the synthesizer 27 computes RGB luminance values (M, M−N, M−N) for red, green and blue color elements. If any of the computed RGB luminance values become negative, the value is forcibly set to zero.

The above computation shows that, for example, when M=10 and N=0, R,G,B=(10,10,10)(refer to P1 in FIG. 9); when M=40 and N=20, R,G,B=(40,20,20)(refer to P2 in FIG. 9); when M=0 and N=30, R,G,B=(0,0,0)(refer to P3 in FIG. 9); and when M=60 and N=40, R,G,B=(60,10,10)(refer to P4 in FIG. 9), respectively.

Accordingly, it is understood that the luminance value of red depends on only that of each pixel of a normal B-mode image. If the luminance value of a certain pixel of a normal B-mode image is zero, that of the superposed image also becomes zero. On the contrary, the luminance values of green and blue are reduced dependently on the luminance of each pixel of a harmonic-mode image. For example, in the case that the luminance value of a certain pixel of a harmonic-mode image is zero, the RGB luminance value of the pixel of the superposed image are (M,M,M) equivalent to the luminance value M of the pixel of a normal B-mode image. In cases where the luminance value of a harmonic-mode image becomes higher, the color tone of red is more intensified, such as R,G,B(60,2,2).

Alternatively, the luminance value of green or blue may be changed in the same manner as discussed above, if a blood distribution is expressed in green or blue in the harmonic-mode image. As a result, harmonics (representing the kinetics of a blood flow) can be acquired as color information while fine image quality that is of the same level as the image quality provided by the normal B-mode is retained.

Figure 11:
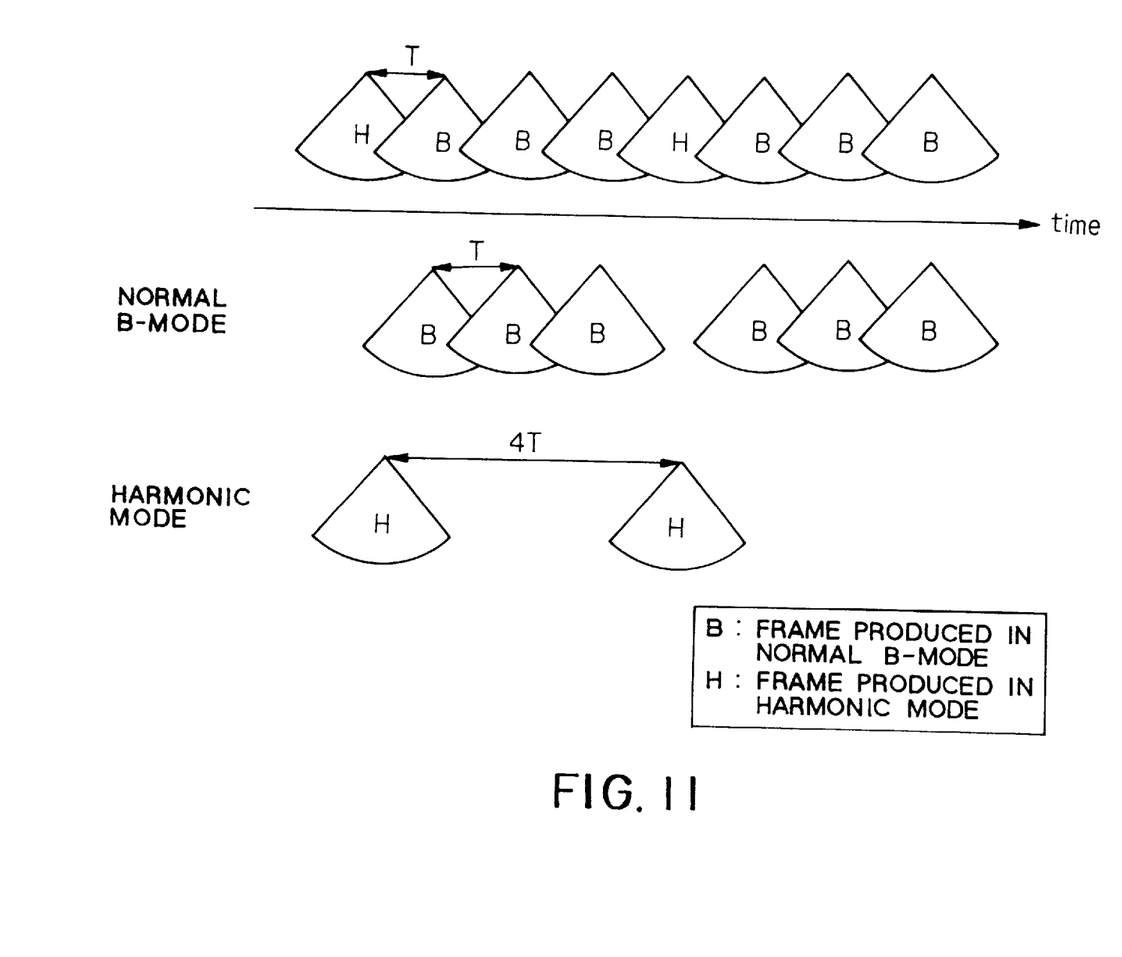
FIG. 11 is a diagram showing a variant of scan control for two modes.

FIG. 11 shows another variant. This variant relates to control of a scanning sequence in each mode. In this embodiment, the harmonic-mode scan and normal B-mode scan are executed alternately for each scanning line. When the tracing of a given number of scanning lines is completed, image data acquired in both the modes is produced. This variant is an example of the diversification of this scanning method.

Fundamentally, scans (for example, 120 scans) required for producing one frame are carried out continuously by changing the direction of a scanning line mode by mode. When scans required for producing one frame in one mode are completed, scans required for producing one frame in the other mode are carried out. However, various variations can be made in terms of the number of pictures of each mode or the order of pictures to be combined. For example, as shown in FIG. 11, there is a method in which, after harmonic-mode pictures constituting one frame are produced, normal B-mode pictures constituting three frames are produced, and this sequence is repeated.

In the case of scan control shown in FIG. 11, assuming that the time required for producing one frame is T [sec.], a harmonic-mode frame is produced at intervals of 4T [sec.]. This makes it possible to perform time adjustment on the speed at which a contrast medium is supplied and the time required for harmonic-mode scan. As mentioned previously, microscopic bubbles of a contrast medium are quite delicate and vanished when irradiated with ultrasonic waves. If bubbles vanish due to irradiated with ultrasonic waves at a rate higher than the speed at which a contrast medium is supplied, harmonics may be reduced or may not be acquired at all. However, according to the variant shown in FIG. 11, a harmonic-mode frame is produced at intervals of 4T [sec.]. The time spacing between scans can be increased. As a result, sufficient microscopic bubbles can be supplied to a region of interest, and harmonics can be acquired satisfactorily. In this case, preferably, the frequency of driving voltage pulses generated in the normal B-mode is set to a value different from the value of the frequency of driving voltage pulses generated in the harmonic mode so that as many microscopic bubbles (of which generation depends on the size of an incident ultrasonic beam) bringing about an acoustic nonlinear phenomenon in the harmonic mode as possible can remain unbroken against normal transmission.

Figure 12:
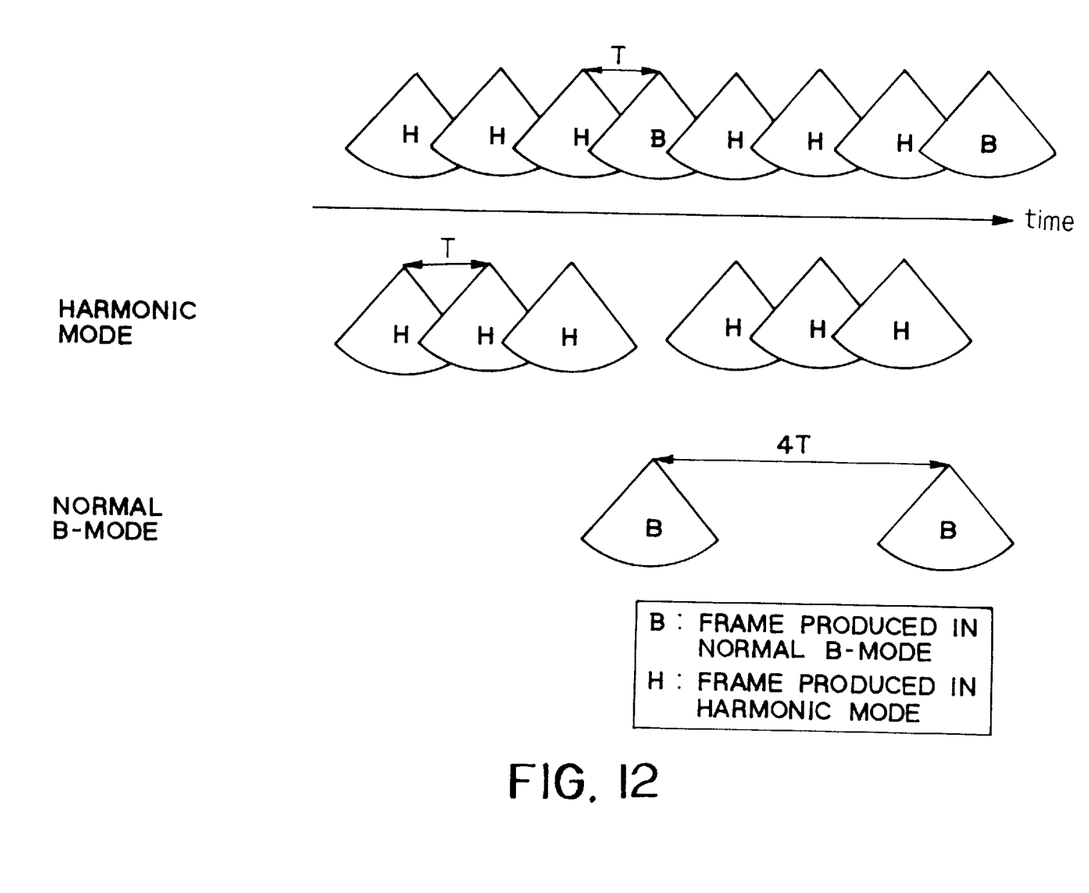
FIG. 12 is a diagram showing another variant of scan control for two modes

In contrast, instead of the scan control shown in FIG. 11, scan control can be carried out based on the sequence shown in FIG. 12. In FIG. 12, the scan control is executed so that a plurality of frames (for example, three frames) of the harmonic-mode images are followed by one frame of the normal B-mode image, which is opposite to the scan control of FIG. 11. In this case, transmitting power of the ultrasonic beam signal is set to conventional values, with the number of transmissions is lowered as much as possible in order to avoid the bubbles of the ultrasonic contrast medium from vanishing.

Still further, in the foregoing embodiments and variations, the sound pressure and/or the transmitting aperture of the probe in the normal B-mode imaging may be lowered relative to the harmonic-mode imaging, when an ultrasonic contrast medium is used, the bubbles of which are fragile to the sound pressure of ultrasonic beam signals of changed transmission frequencies.

Still, one of the most important and essential matters of the invention is to alter the scan conditions for each raster between the normal B-mode and the harmonic mode. Thus, the two pulsers 54B and 54H in FIG. 1 may be replaced by other means, such as parameter control means (for example, CPU), to one pulser (without two pursers), for exchanging at least one of the scan parameters shown in FIG. 5 between the two modes. The invention includes such modified embodiment.

For the sake of completeness it should be mentioned that the embodiments and variants shown above are not definitive lists of the invention. The expert will appreciate that it is possible to supplement or modify them by measures known from the prior art without departing from the basic inventive principle.

What is claimed is:

1. A diagnostic ultrasound system concurrently providing a first tomographic image indicative of a tissue residing in a cross section of an object and a second tomographic image indicative of a distribution of blood flowing in the tissue residing in the cross section using harmonic contrast agent, the system comprising:

means for repetitively scanning an ultrasonic signal along the cross section of the object so as to form a plurality of successive frames of scanning, said scanning means including means for controlling the scan so that the ultrasonic signal is scanned automatically and alternatively for each of a first imaging mode for obtaining the first tomographic image and a second imaging mode for obtaining the second tomographic image, said means for controlling further including means for automatically setting individual optimum transmitting conditions for each of the first and second imaging modes soas to minimize bubble collapse of said harmonic contrast agent;

means for acquiring an echo of the ultrasonic signal reflected from the cross section;

first means for producing image data of the first tomographic image on the basis of the echo;

second means for producing image data of the second tomographic image on the basis of the echo; and means for visualizing the image data of the first and second tomographic images.

2. The system of claim 1, wherein said scan-controlling means includes means that cause the scan in the second imaging mode to precede the scan in the first imaging mode.

3. The system of claim 2, wherein said visualizing means comprises a monitor and means for displaying the image data of the first and second tomographic images on the monitor as a pair of dual images.

4. The system of claim 2, wherein said visualizing means comprises a monitor and means for superimposedly displaying the image data of the second tomographic image on the image data of the first tomographic image on the monitor as a single image.

5. The system of claim 4, wherein said displaying means includes an element for providing a color for the image data of the second tomographic image.

6. The system of claim 4, wherein said displaying means includes an element for pixel by pixel masking the image data of the second tomographic image with the image data of the first tomographic image.

7. The system of claim 2, wherein said scan-controlling means includes an element repeating the scan for each raster alternately and automatically between the first and second imaging modes during one time of scanning over the cross section, each raster being formed in the cross section by the transmitted ultrasonic signal, and an element causing the scan in the second imaging mode to precede the scan in the first imaging mode for each raster.

8. The system of claim 2, wherein said scan-controlling means includes an element automatically switching the scan between the first and second imaging modes frame by frame and an element causing the scan in the second imaging mode to precede the scan in the first imaging mode.

9. The system of claim 8, wherein said switching element includes an element switching both of the scan in the first imaging mode and the scan in the second imaging mode automatically and alternately.

10. The system of claim 7, wherein said switching element includes an element performing switching between the scan in the second imaging mode for one frame and the scan in the first imaging mode for more than one frame.

11. The system of claim 2, wherein said individual optimum transmitting conditions include a sound pressure of the ultrasonic signal and at least one of a transmission frequency of the ultrasonic signal, the number of waves of the ultrasonic signal, a waveform of the ultrasonic signal, a focal point of the ultrasonic signal, a transmission rate of the ultrasonic signal, and a transmission aperture of an ultrasonic probe transmitting the ultrasonic signal.

12. The system of claim 11, wherein said transmitting conditions include the transmission frequency and the second imaging mode is smaller in the transmission frequency than the first imaging mode.

13. The system of claim 11, wherein the second imaging mode is smaller in the sound pressure than the first imaging mode.

14. The system of claim 11, wherein said transmitting conditions include the transmission aperture and the second imaging mode is smaller in the transmission aperture than the first imaging mode.

15. The system of claim 11, wherein said the transmitting conditions include the number of waves and the second imaging mode is greater in the number of waves than the first imaging mode.

16. The system of claim 11, wherein said transmitting conditions include the waveform and the second imaging mode is smaller than the first imaging mode in a non-fundamental frequency component included in the waveform.

17. The system of claim 11, wherein said transmitting conditions include setting the focal point deeper in the second imaging mode than in the first imaging mode.

18. The system of claim 11, wherein said transmitting conditions includes setting the transmission rate smaller in the second imaging mode than in the first imaging mode.

19. The system of claim 18, wherein said transmitting conditions include setting the transmission rate smaller in the second imaging mode than in the first imaging mode.

20. The system of claim 2, wherein the second producing means includes a first element which extracts from a signal of the echo a signal of a non-fundamental frequency component other than a fundamental frequency component of the ultrasonic signal and a second element which produces the image data of the second tomographic image based on the extracted signal.

21. A diagnostic ultrasound system concurrently providing a first tomographic image indicative of a tissue residing in a cross section of an object and a second tomographic image indicative of a distribution of blood flowing in the tissue residing in the cross section using a harmonic contrast agent, the system comprising:

an ultrasonic probe transmitting an ultrasonic signal to the object and receiving an echo of the ultrasonic signal reflected from the object;

an ultrasonic transmitting unit including a first pulser for driving the ultrasonic probe in a first imaging mode for obtaining the first tomographic image and a second pulser for driving the ultrasonic probe in a second imaging mode for obtaining the second tomographic image;

a switch for selectively activating either one of the first and second pulsers in the ultrasonic transmitting unit;

a control unit for controlling the scan so that the ultrasonic signal is scanned automatically and alternatively for each of the first and second imaging modes, said means for controlling further including means for automatically setting individual optimum transmitting conditions for each of the first and second imaging modes soas to minimize bubble collapse of said harmonic contrast agent;

an ultrasonic receiving unit for receiving a signal of the echo and executing a predetermined process on the signal of the echo;

a processing unit for producing image data of the first and second tomographic images from the processed signal of the echo; and a display for displaying the image data.

22. The system of claim 21, wherein the control unit includes a control element causing the scan in the second imaging mode to precede the scan in the first imaging mode.

23. The system of claim 22, wherein said control element is configured to repeat the scan for each raster automatically and alternately between the first and second imaging modes each raster being formed by the ultrasonic signal in the cross section.

24. The system of claim 22, wherein said transmission conditions include a sound pressure of the ultrasonic signal and at least one of a transmission frequency of the ultrasonic signal, the number of waves of the ultrasonic signal, a waveform of the ultrasonic signal, a focal point of the ultrasonic signal, a transmission rate of the ultrasonic signal, and a transmission aperture of the ultrasonic probe.

25. The system of claim 24, wherein said the transmitting conditions include the transmission frequency and the second imaging mode is smaller in the transmission frequency than the first imaging mode.

26. The system of claim 24, wherein the second imaging mode is smaller in the sound pressure than the first imaging mode.

27. The system of claim 24, wherein said the transmitting conditions include the number of waves and the second imaging mode is greater in the number of waves than the first imaging mode.

28. The system of claim 24, wherein said transmitting conditions include the transmission aperture and the second imaging mode is smaller in the transmission aperture than the first imaging mode.

29. The system of claim 24, wherein said transmitting conditions include the waveform and the second imaging mode is smaller than the first imaging mode in the non-fundamental frequency component included in the waveform.

30. The system of claim 24, wherein said transmitting conditions include setting the focal point deeper in the second imaging mode than in the first imaging mode.

31. The system of claim 22, wherein said processing means includes a circuit superimposing the image data of the second tomographic image on the image data of the first tomographic image and wherein said display displays the superimposed image data.

32. The system of claim 22, wherein the ultrasonic receiving unit includes an element extracting from a signal of the echo a signal of a non-fundamental frequency component other than a fundamental frequency component of the ultrasonic signal and the processing unit includes an element producing the image data of the second tomographic image based on the extracted signal.

* * * * *